United States Patent
Sum et al.

(10) Patent No.: US 8,000,774 B2
(45) Date of Patent: Aug. 16, 2011

(54) METHOD AND SYSTEM FOR INTRA LUMINAL THROMBUS DETECTION

(75) Inventors: Stephen Thomas Sum, Waltham, MA (US); Jennifer Blanche Lisauskas, Brighton, MA (US); Thomas M. Meese, Somerville, MA (US)

(73) Assignee: Infraredx, Inc., Burlington, MA (US)

( * ) Notice: Subject to any disclaimer, the term of this patent is extended or adjusted under 35 U.S.C. 154(b) by 198 days.

(21) Appl. No.: 11/619,387

(22) Filed: Jan. 3, 2007

(65) Prior Publication Data

US 2008/0161698 A1    Jul. 3, 2008

(51) Int. Cl.
*A61B 6/00* (2006.01)

(52) U.S. Cl. ........ 600/473; 600/431; 600/443; 600/476; 600/509; 356/476

(58) Field of Classification Search .......... 600/407–480, 600/481, 326
See application file for complete search history.

(56) References Cited

U.S. PATENT DOCUMENTS

| | | | |
|---|---|---|---|
| 6,394,956 B1 * | 5/2002 | Chandrasekaran et al. | 600/439 |
| 6,485,413 B1 * | 11/2002 | Boppart et al. | 600/160 |
| 6,890,332 B2 * | 5/2005 | Truckai et al. | 606/41 |
| 7,208,190 B2 * | 4/2007 | Verlee et al. | 427/2.24 |
| 2002/0177777 A1 * | 11/2002 | Nordstrom et al. | 600/475 |
| 2002/0183601 A1 | 12/2002 | Tearney et al. | |
| 2003/0028100 A1 * | 2/2003 | Tearney et al. | 600/431 |
| 2003/0055307 A1 * | 3/2003 | Elmaleh et al. | 600/1 |
| 2004/0073120 A1 * | 4/2004 | Motz et al. | 600/478 |
| 2005/0043637 A1 | 2/2005 | Caplan et al. | |
| 2006/0041199 A1 * | 2/2006 | Elmaleh et al. | 600/478 |
| 2007/0038124 A1 * | 2/2007 | Fulghum et al. | 600/476 |
| 2007/0258906 A1 * | 11/2007 | Fischman et al. | 424/9.71 |

FOREIGN PATENT DOCUMENTS

| WO | 2004/012586 A2 | 2/2004 |
|---|---|---|
| WO | 2005/096921 A1 | 10/2005 |

OTHER PUBLICATIONS

"MGH and CIMIT Researchers Use Laser Light to Identify Atherosclerotic Plaques That Cause Heart Attacks," Healthcare Sales & Marketing Network NewsFeed, http://www.salesandmarketingnetwork.com/news_release.php?ID=2006424&key=laser, 2 pages, News Release, Aug. 1, 2005.

Nadkarni, Seemantini K., et al., "Characterization of Atherosclerotic Plaques by Laser Speckle Imaging," Circulation 112(6):885-92. Aug. 9, 2005.

(Continued)

*Primary Examiner* — Brian Casler
*Assistant Examiner* — Nasir Shahrestani
(74) *Attorney, Agent, or Firm* — Rothwell, Figg, Ernst & Manbeck, PC (57) ABSTRACT

A method for detecting a complete or partial obstruction in a vessel through an intervening fluid includes receiving spectroscopic responses at different locations of a vessel wall, e.g., a vein or artery, through an intervening fluid, preferably blood. Spectroscopic responses are generated by irradiating the vessel wall at different locations and detecting spectra at those locations. In preferred embodiments, the radiation used is in the near infrared (NIR) region of the electromagnetic spectrum. The thrombus is located by determining whether fluctuations, spatial and/or spectral, of the spectral responses are indicative of thrombus.

16 Claims, 7 Drawing Sheets

OTHER PUBLICATIONS

Nadkarni, Seemantini K., et al., "Measurement of fibrous cap thickness in atherosclerotic plaques by spatiotemporal analysis of laser speckle images," Journal of Biomedical Optics, vol. 11, No. 2, pp. 021006-1 to 021006-8, Mar./Apr. 2006.

Caplan, Jay D., et al., "Near-Infarared Spectroscopy for the Detection of Vulnerable Coronary Artery Plaques," Journal of the American College of Cardiology, vol. 47, No. 8, Suppl C, Apr. 18, 2006, pp. C93-C96.

International Search Report from PCT/US2007/084416, filed on Nov. 12, 2007.

Written Opinion of the International Searching Authority from PCT/US2007/084416, filed on Nov. 12, 2007.

* cited by examiner

METHOD AND SYSTEM FOR INTRA LUMINAL THROMBUS DETECTION

BACKGROUND OF THE INVENTION

Intra luminal spectroscopic analysis devices have been developed and commercialized. One application concerns the assessment of the state of blood vessel walls such as required in the diagnosis of atherosclerosis. This is an arterial disorder involving the intimae of medium- or large-sized arteries, including the aortic, carotid, coronary, and cerebral arteries. Atherosclerotic lesions or plaques can contain complex tissue matrices, including collagen, elastin, proteoglycans, and extracellular and intracellular lipids with foamy macrophages and smooth muscle cells. In addition, inflammatory cellular components (e.g., T lymphocytes, macrophages, and some basophiles) can also be found in these plaques.

The intra luminal spectroscopic analysis devices are used to extract information concerning the state of the vessels walls from the generated spectral information. Mathematical and statistical manipulations such as linear and non-linear regressions of the spectral band of interest and other multivariate analysis tools are available for building quantitative calibrations as well as qualitative models for discriminant analysis, enabling the detection and characterization of any vascular lesions.

One specific intra luminal spectroscopic analysis device uses an optical source, such as a tunable laser, to access or scan a spectral band of interest, such as a scan band in the near infrared of 750 nanometers (nm) to 2.5 micrometers ($\mu$m). The generated light is used to illuminate tissue in a target area in vivo using a catheter. Diffusely reflected light resulting from the illumination is then collected and transmitted to a detector system, where a spectral response is resolved.

This intra luminal spectroscopic device actually builds a "color picture" of the inner walls of the blood vessel. This is accomplished by rotating the head of the catheter while drawing the head through the region of interest of the vessel. This produces the spectral response within the scan band of the tunable laser for a series of points along a helical path across the vessels walls. These points are aligned into a raster image of the vessel wall for the region of interest.

Another potential problem associated with vessels is the formation of thrombus. A thrombus or blood clot is a product of coagulation within a blood vessel and typically appears as a semisolid mass, with the thrombus impeding or blocking the flow of blood through the vessel. Typically it includes platelets, red blood cells, white blood cells and/or fibrin. Thrombosis, i.e., the formation or presence of a clot or thrombus, can be caused by infection, trauma, injury, a slowing down or stagnation of blood flow past a point of injury, or rupture of an atherosclerotic plaque. In fact, disruption or rupture of atherosclerotic plaques appears to be the major cause of heart attacks and strokes, because, after the plaques rupture, local obstructive thromboses form within the blood vessels. Both venous and arterial thrombosis can occur. A coronary thrombus often initially forms at the site of rupture of a vulnerable plaque; i.e. at the location of a plaque with a lipid-rich core and a thin fibrous cap (thin-cap fibroatheroma or TCFA). Thus, locating a thrombus can help find the culprit lesion, a task that is difficult using the current practice of angiography when the lesion is non-stenotic. Approaches for managing thrombosis include treatment with anticoagulants and/or medication designed to dissolves the clot, bed rest or surgical removal.

SUMMARY OF THE INVENTION

The invention generally relates to detecting a complete or partial obstruction in a vessel through an intervening fluid. In one example, the obstruction is a thrombus. In vivo location of a thrombus is useful during diagnosis, in monitoring response to medication, and in surgical procedures.

In one aspect of the invention, locating a thrombus includes receiving spectroscopic responses of a vessel wall, e.g., a vein or artery, through an intervening fluid, preferably blood. Saline solution or another suitable fluid also can be employed.

Spectroscopic responses are generated by irradiating the vessel wall at different locations and detecting spectra at those locations. In preferred embodiments, the radiation used is in the near infrared (NIR) region of the electromagnetic spectrum. As used herein, NIR refers to electromagnetic radiation in the wavelength region of about 700 nanometers (nm) to about 3000 nm.

In some implementations, the spectral response is first acquired for a full spectral region and then bands selected within the full spectral region for further analysis. NIR can be generated by a tunable laser.

In general according to one aspect, the invention features a method for locating a vascular obstruction. The method comprises determining spectroscopic responses within different regions of a wall of a vessel through an intervening fluid and analyzing spatial fluctuations in the spectral responses in the different regions. Any vascular obstruction is then located to one or more of the regions based on the spatial fluctuations in the spectral responses.

In embodiments, the step of determining the spectroscopic responses comprises irradiating the different regions with a near infrared source and detecting diffuse reflectance spectra within the different regions. Also, the step of determining the spectroscopic responses comprises irradiating the different regions with a near infrared source and detecting absorption spectra within the different regions. In the typical example, a catheter is inserted into the vessel, which is irradiated via a head of the catheter. The returning light is detected while rotating the head within the vessels and drawing the head through the vessel to generate a helical raster scan.

Preferably, the step of analyzing the spatial fluctuations further comprises determining regions in which the spatial fluctuations of the spectral response exceed a threshold, possibly in a narrowed wavelength band, such as one in which lipids have strong reflectance.

In general according to another aspect, the invention features device for locating vascular obstructions. This device comprises an optical catheter that is inserted into a blood vessel and a spectrometer for generating light into and receiving light from the optical catheter to resolve spectral responses of walls of the blood vessel. An analyzer receives the spectral responses and searches for regions of the walls of the blood vessels that exhibit spatial fluctuations in the spectral responses to locate vascular obstructions to the regions based on the spatial fluctuations in the spectral responses.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1A:
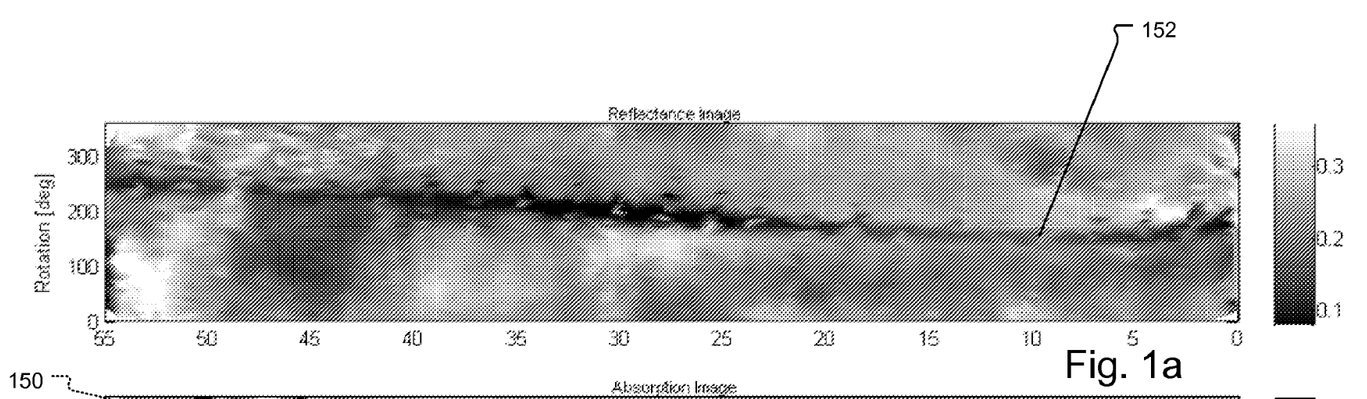
FIGS. 1a and 1b show a reflectance image and an absorption image, respectively, generated by the near infrared (NIR) scanning of the inside of a blood vessel covering a pullback distance of 0 to 55 millimeters and an angular range of 0 to 360 degrees.
Figure 1B:
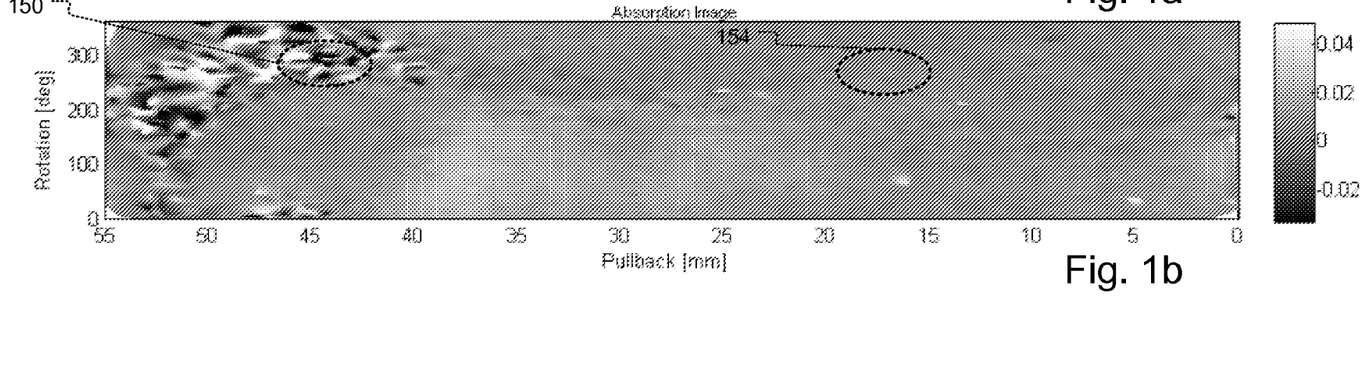

FIGS. 1a and 1b show a reflectance image and an absorption image generated by the near infrared (NIR) scanning of the inside of a blood vessel. These spectral measurements were collected through flowing blood.

The guide wire 152 can be seen as a dark shadow across the mean reflectance pullback image in FIG. 1a. For this image, an average of the reflectance spectrum across the full wavelength range is taken for each pixel. Thus, each pixel in the image is the average intensity of the reflectance spectrum at that point.

FIG. 1b is notable because it shows a distinct mottled pattern in regions including region 150 in the peak absorbance image at a pull back distance of approximately 40-55 millimeters corresponding to the location of an obstruction, such as a clot or thrombus. The absorption image is referred to as "peak absorbance" because here the average of each pixel is taken across a limited wavelength range (1200-1240 nm) where lipids have a strong absorbance signal or peak. The average here can be thought of an approximate area under the peak since it is taken after a linear baseline correction.

Figure 2A:
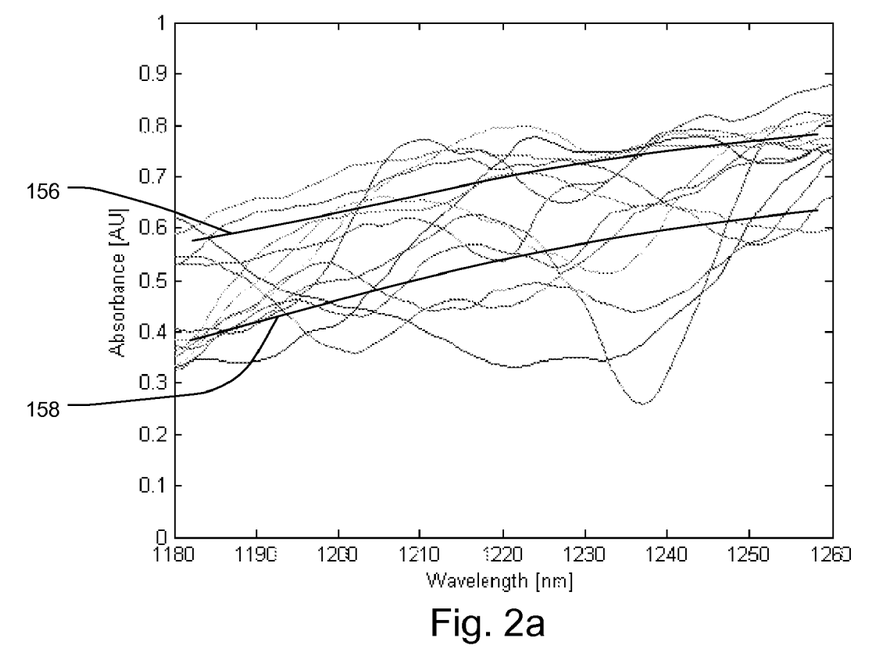
FIGS. 2a and 2b are plots of absorbance as a function of wavelength for various pixels within regions 150 and 154, respectively, in FIG. 1b.
Figure 2B:
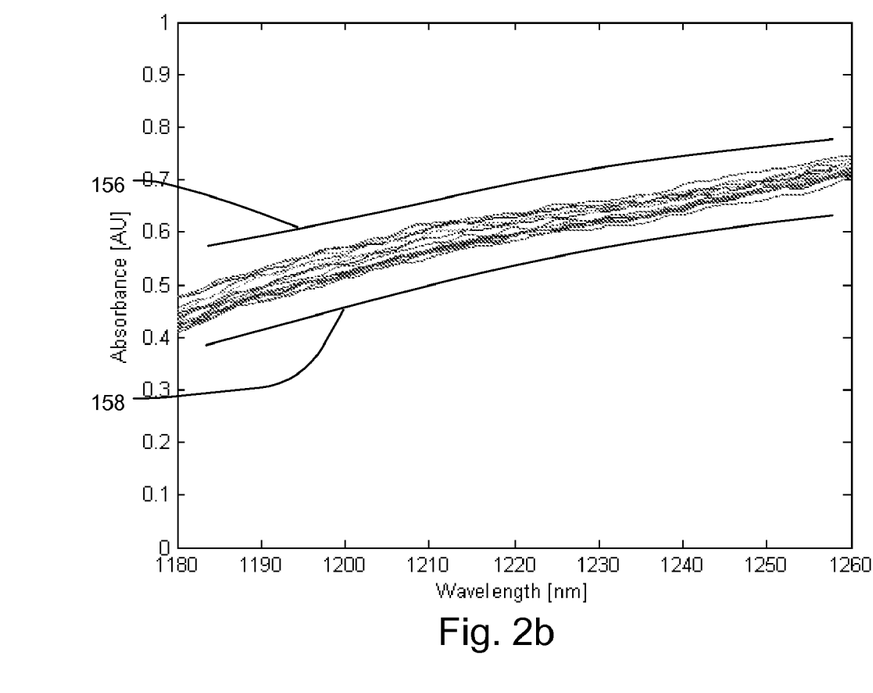

FIGS. 2a and 2b further characterize the differences between the mottled region 150 at 42-45 millimeters and 275 to 300 degrees in FIG. 1b and the typical spectral characteristics of the vessel walls such as exemplified in pullback region 15-18 millimeters and angle 275 to 300 degrees in FIG. 1b. The mottled spectra of the thrombus have significantly different characteristics from the spectra taken from the normal regions.

Specifically, the absorbance as a function of wavelength for various pixels within mottled region 150, for example, is plotted in FIG. 2a. It shows a high degree of variation or spectral and spatial fluctuation in the spectral responses. In more detail, each plotted pixel in FIG. 2a exhibits large "intra-pixel" variation in its spectral response over the 1180 to 1260 spectral band that is plotted. That is, each line in FIG. 2a shows large departures from an average response. Moreover, FIG. 2a exhibits a large "inter-pixel" variation in that the spectral responses for the various pixels are very different from each other with a low degree of inter-pixel correlation.

The intra-pixel and inter-pixel variation of FIG. 2a is in contrast to pixels of region 154 plotted in FIG. 2b. Here the spectral response of each pixel is very smooth, almost linear over the 1180-1260 scan band, a low degree of intra-pixel spectral variation over the scan band. Also the spectral responses of the plotted pixels are very similar to each other, a low degree of inter-pixel variation. Experimentation and observation has shown that these regions of high spatial and high pixel fluctuation in the spectral responses are associated with obstructions, such as thrombi, on the inner walls of the vessel.

In one embodiment, the absorbance as a function of wavelength for individual pixels and/or pixels within a region are compared to an average absorbance at each wavelength, and specifically an upper threshold 156 and a lower threshold 158, which are set based on the calculated average absorbance. When the absorbance of a pixel or pixels within a region repeatedly fall outside these thresholds, the region is said to be mottled and a potential area of a thrombus.

In another approach, for detecting inter-pixel variation, a fixed-size rectangular window (pullback position range in millimeters and angular position range in degrees) is sequentially moved along the longitudinal and rotational angle directions of the pullback. At each window position, absorbance spectra corresponding to the locations within the window are averaged to give a single mean absorbance spectrum. An nth order polynomial function is then fitted to the mean absorbance spectrum and the absorbance difference at each wavelength between the measured and fitted spectrum is computed. A score for the window is determined by calculating the root mean square (RMS) of the absorbance differences. The window is then translated by a fixed amount and the scoring process repeated. Scores are thus computed for each window position across the pullback. Regions with high scores are said to be mottled and potential areas of thrombus.

In still another approach, for detecting intra-pixel variation, pixels are sequentially selected. For each pixel, nth, such as $1^{st}$ or $2^{nd}$, order polynomial function is fitted to the absorbance spectrum for the pixels and the absorbance difference at each wavelength between the measured and fitted spectrum is computed. A score for the pixel is determined by calculating the root mean square (RMS) of the absorbance differences. Based on a single pixel score or the scores of a group of adjacent pixels, individual pixels or groups of pixels with high scores are said to be mottled and potential areas of thrombus.

Figures 3A, 3B:
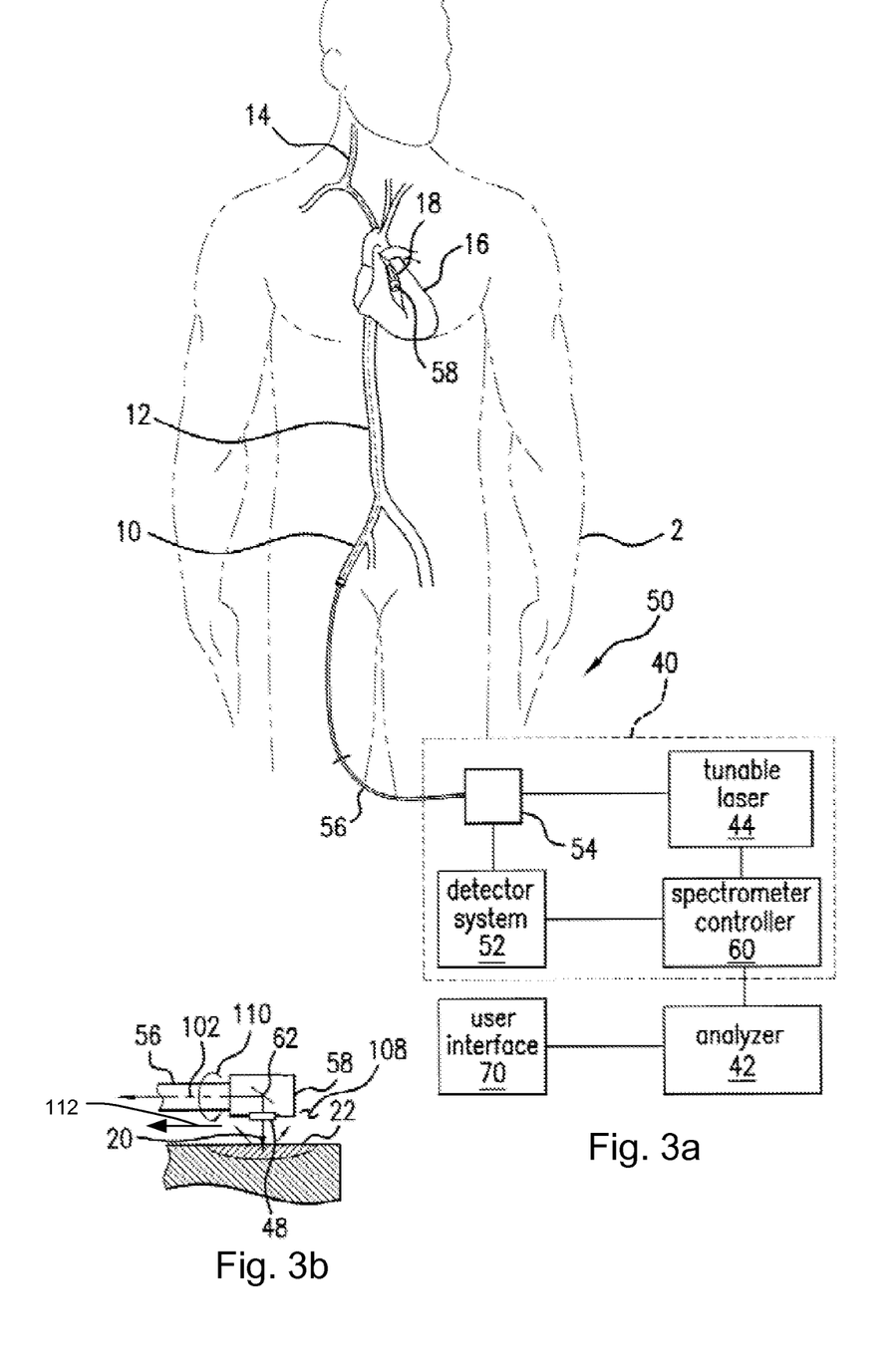
FIGS. 3a and 3b illustrate a device for detecting and analyzing the spectral responses of the vessel walls including detection of thrombus according to the invention.

FIGS. 3a and 3b illustrate an exemplary device for detecting and analyzing the spectral responses of the vessel walls.

The device generally comprises a catheter 56, a controller 40, and analyzer 42. In more detail, the catheter 56 includes the optical fiber bundle. The catheter 56 is typically inserted into the patient 2 via a peripheral vessel, such as the femoral artery 10. The catheter head 58 is then moved to a desired target area, such as a coronary artery 18 of the heart 16 or the carotid artery 14. In the embodiment, this is achieved by moving the catheter head 58 up through the aorta 12. In many cases, the catheter rides on a guide wire that is first advanced through the patient's blood vessels.

When at the desired site, radiation is generated. In the current embodiment optical radiation is generated, preferably by a tunable source 44, such as a semiconductor tunable laser, and tuned over a range covering one or more spectral bands of interest. In other embodiments, one or more broadband sources are used to access the spectral bands of interest. In either case, the optical signals are coupled into the single mode fibers of the catheter 56 to be transmitted to the catheter head 58.

In the current embodiment, optical radiation in the near infrared (NIR) spectral regions is used for spectroscopy. Exemplary scan bands include 1000 to 1450 nanometers (nm) generally, or 1000 nm to 1350 nm, 1150 nm to 1250 nm, 1175 nm to 1280 nm, and 1190 nm to 1250 nm, more specifically. Other exemplary scan bands include 1660 nm to 1740 nm, and 1630 nm to 1800 nm.

However, in other optical implementations, scan bands appropriate for fluorescence and/or Raman spectroscopy are used. In still other implementations, scan bands in the visible or ultraviolet regions are selected.

In the current embodiment, the returning light is transmitted back down multimode optical fibers of the catheter 56. The returning radiation is provided to a detector system 52, which can comprise one or multiple detectors.

A spectrometer controller 60 monitors the response of the detector system 52, while controlling the source or tunable laser 44 in order to probe the spectral response of a target area, typically on an inner wall of a blood vessel and through the intervening blood or other unwanted signal source, which is typically a fluid, such as a saline flush.

As a result, the spectrometer controller 60 is able to collect spectra. When the acquisition of the spectra is complete, the spectrometer controller 60 then provides the data to the analyzer 42.

With reference to FIG. 3b, the optical signal of the tunable laser 44 is carried by fiber bundle 102 and directed by the side firing termination 62, to exit from the catheter head 58 through window 48 and impinge on the target area 22 of the artery wall 24. The catheter head 58 then collects the light that has been diffusely reflected or refracted (scattered) from the target area 22 and the intervening fluid 108 through window 48 and returns the light in bundle 102 back down the catheter 56 through the multimode fibers to the detector system 52.

In one embodiment, the catheter head 58 spins as illustrated by arrow 110. This allows the catheter head 58 to scan a complete circumference, 0-360 degrees, of the vessel wall 24. Also, the head 58 is pulled back in direction of arrow 112. This combined rotation and longitudinal movement allow a portion or section of the vessel to be analyzed by creating a helical raster scan of the inner vessel walls. Specifically, the movement 110, 112 of the catheter head 58 is driven by a pullback and rotation unit 54 that draws the catheter head 58 longitudinally through the vessel such as the coronary or carotid artery, and also drives the catheter head 58 to rotate within that vessel.

Generally, the analyzer 42 makes an assessment of the state of the blood vessel walls 24, which is presented to the operator via interface 70. The collected spectral response is used to determine whether each region of interest 22 of the blood vessel wall 24 comprises a lipid pool or lipid-rich atheroma, a disrupted plaque, a vulnerable plaque or thin-cap fibroatheroma (TCFA), a fibrotic lesion, a calcific lesion, and/or normal tissue. Each region 22 is also analyzed for the presence of an obstruction, such as thrombosis in the current application. This categorized or even quantified information is provided to an operator via a user interface 70, or the raw collected spectral images are provided to the operator, who then makes the conclusion as to the state of the region of interest 22.

According to the invention, the analyzer 42 searches for pixels, groups of pixels, or pixels within regions of the vessel walls that exhibit spatial fluctuations in the spectral responses and specifically those regions in which the spatial fluctuations of the spectral response fall outside thresholds 156 and/or 158. By identifying these regions, the analyzer 42 locates any thrombi or presents the images including the peak absorbance images to the operator, who then finds the spatial fluctuations indicative of thrombi.

Figure 4:
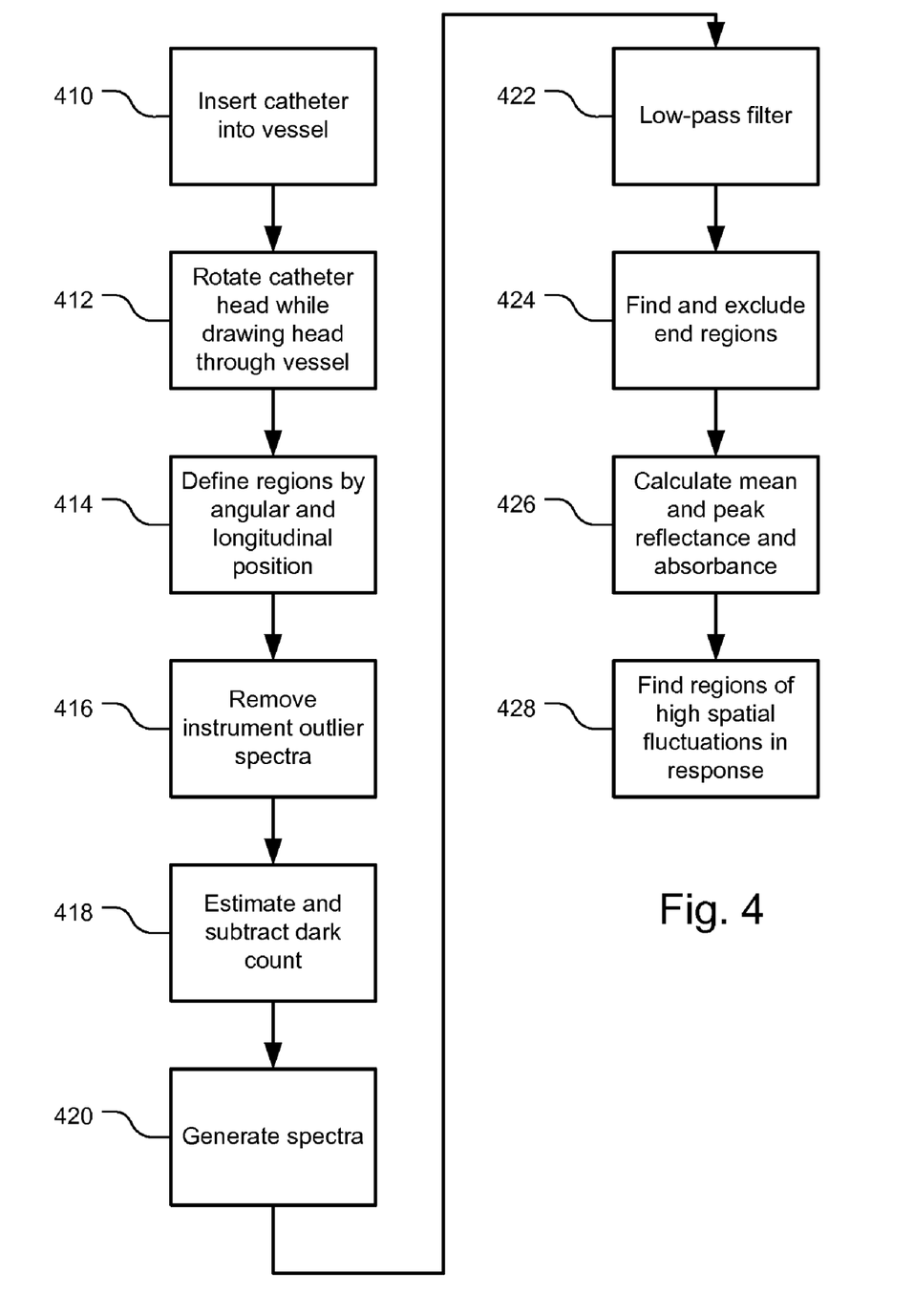
FIG. 4 is a flow diagram showing a method for detecting thrombus according to the present invention.

FIG. 4 is a flow diagram illustrating a process for detecting thrombus in the blood vessels.

Specifically, in step 410, the catheter 56 is inserted into the vessel 14, 18 of interest. Then, the pullback and rotation unit 54 drives the catheter head 58 to rotate within the vessel while the head 58 is drawn through the vessel in step 412. This produces the helical scans and specifically the NIR spectra of the inner walls.

Then in step 414, the helical scans are compiled into images that define regions relative to angular position, i.e., the angular position of the head, and the longitudinal position of the head, during the scan. This produces the images as shown in FIGS. 1a and 1b.

These images are then processed in order to locate any potential thrombus. Specifically, in a first processing step 416, the spectra are analyzed to remove any artifacts introduced by instrument operation. Specifically, data associated with improper operation of the instrument are removed as being data acquisition errors.

Then in step 418, a dark count estimation and subtraction is performed on the image. Specifically, an estimation of the dark count for each scan is determined and subtracted from the collected spectra.

In step 420, the reflectance and absorbance spectra are generated. These are generated by calculating the ratio of the dark count corrected signal and a reference spectra.

The collected spectra are then low pass filtered at a 2 nanometer resolution in step 422.

Also, in step 424, end regions of the scan, i.e., data generated initially during the pullback and/or near the end of the pullback are excluded at the extremes of the pullback as being outside the area of interest. In one example, only the proximal end of the pullback is excluded in vivo, and even then only if the catheter head was pulled into the guide catheter. Generally, data corresponding to regions outside of the area of interest, e.g. guide catheter, are excluded.

Mean reflectance and absorbance peak areas are computed in step 426. Specifically, for the entire scans, the mean reflectance across the full wavelength region (1180-1260 nanometers) and the area under the base-line corrected absorbance peak between 1200 and 1240 nanometers are calculated. Then, based upon these mean and standard deviation calculations and also possibly averages, the thresholds 156, 158 or curve fits are determined and the images are analyzed to find pixels or regions such as region 150 where there are high levels of intra-pixel or spatial fluctuation in the spectral responses in step 428. These regions are then further analyzed for the existence of a thrombus.

Figure 5A:
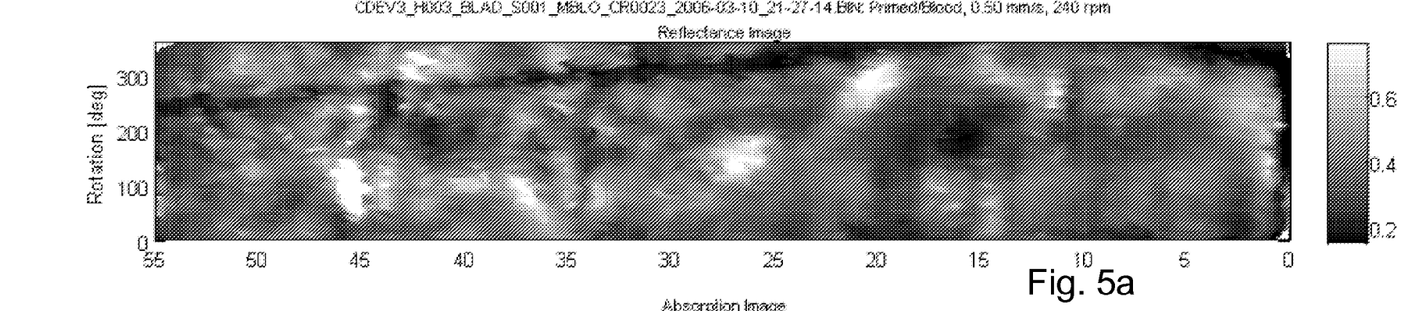
FIGS. 5a and 5b show a reflectance image and an absorption image, respectively, generated by the near infrared (NIR) scanning of the inside of a blood vessel through flowing blood for another blood vessel.
Figure 5B:
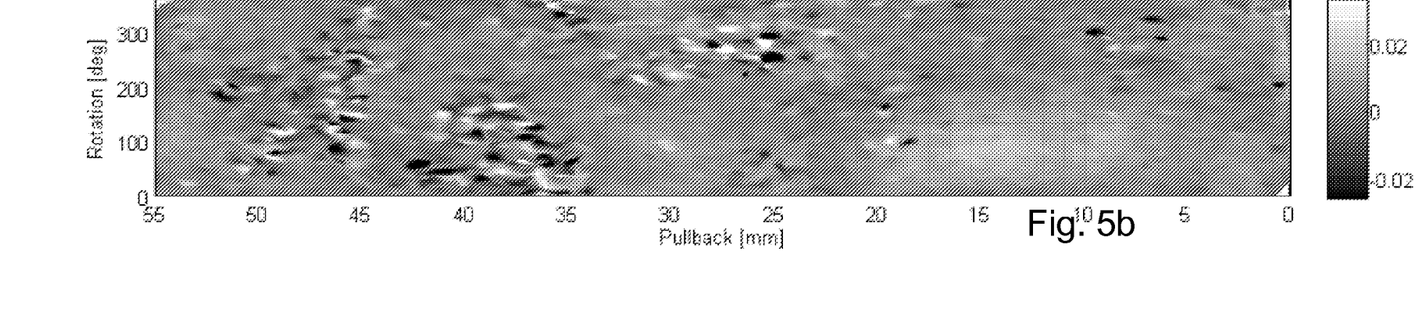

FIGS. 5a and 5b show reflectance and absorption spectra from a pullback through a human coronary artery. FIG. 5a shows the mean reflectance as a function of rotation angle and pullback distance. FIG. 5b shows peak absorbance area (1200-1240 nm) as a function of rotation angle and pullback distance. Spectral measurements are collected through flowing human blood. Thrombus image features are seen at a pullback distance between 34 and 49 millimeters in absorbance image of FIG. 5b.

Figure 6A:
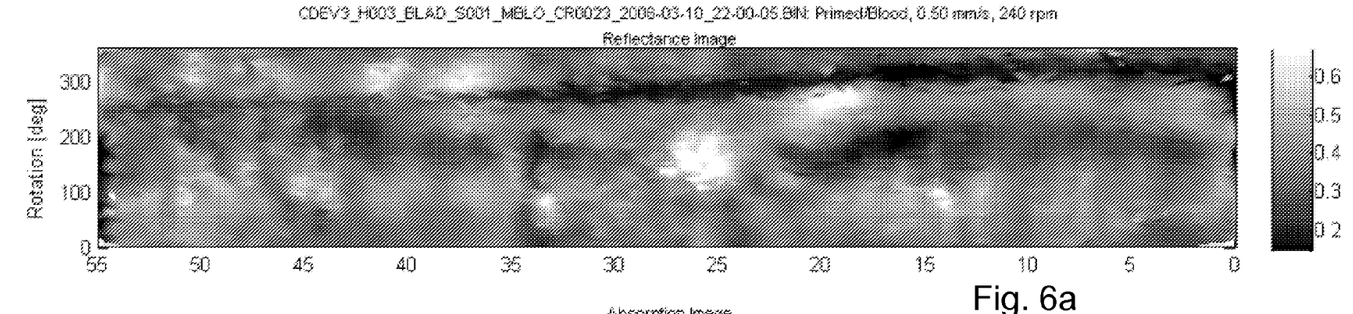
FIGS. 6a and 6b show a reflectance image and an absorption image, respectively, generated by the near infrared (NIR) scanning of the inside of a blood vessel for stagnant blood for the blood vessel used in the generation of the data in FIGS. 5a and 5b.
Figure 6B:
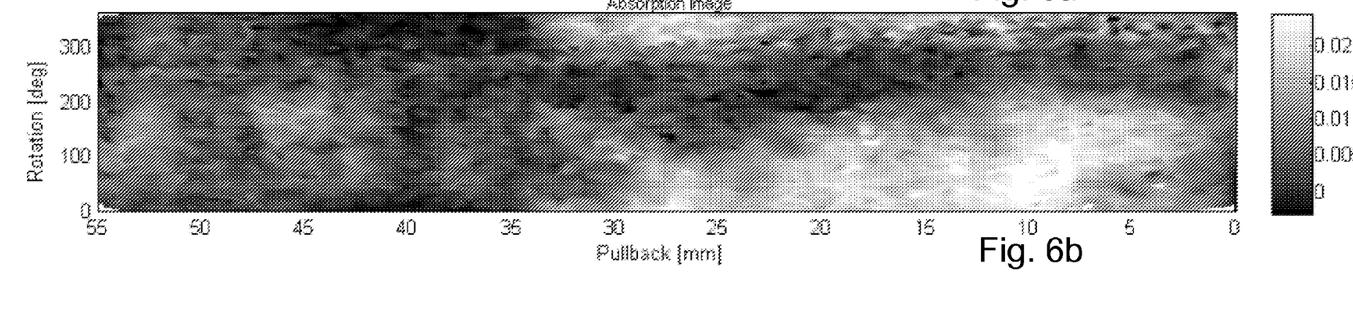

FIGS. 6a and 6b show the reflectance and absorption spectra for the same human coronary artery used to produce FIGS. 5a and 5b. FIG. 6a shows the mean reflectance as a function of rotation angle and pullback distance. FIG. 6b shows peak absorbance area (1200-1240 nm) as a function of rotation angle and pullback distance. Spectral measurements were collected through stagnant human blood. Thrombus image features are no longer seen at a pullback distance between 34 and 44 mm in absorbance image of FIG. 6b. These data suggest that the mottling in the spectral images associated with thrombus area is related to interaction of the obstruction and the flowing blood. The thrombus may act as an obstruction that causes eddies in the flow, thereby altering the NIR scattering properties of the blood. Alternatively, the thrombus may be subject to a fluttering motion by the flow of blood, causing a rapidly varying NIR scattering surface.

The analysis shows that the NIR absorbance measured through flowing blood produced a distinctive mottled pattern that correlated with the presence of thrombus in the vessel wall. The pattern was not visible when blood flow through the vessel was stopped, suggesting that the thrombus has a physical effect on light scatter that is detectable.

Figure 7:
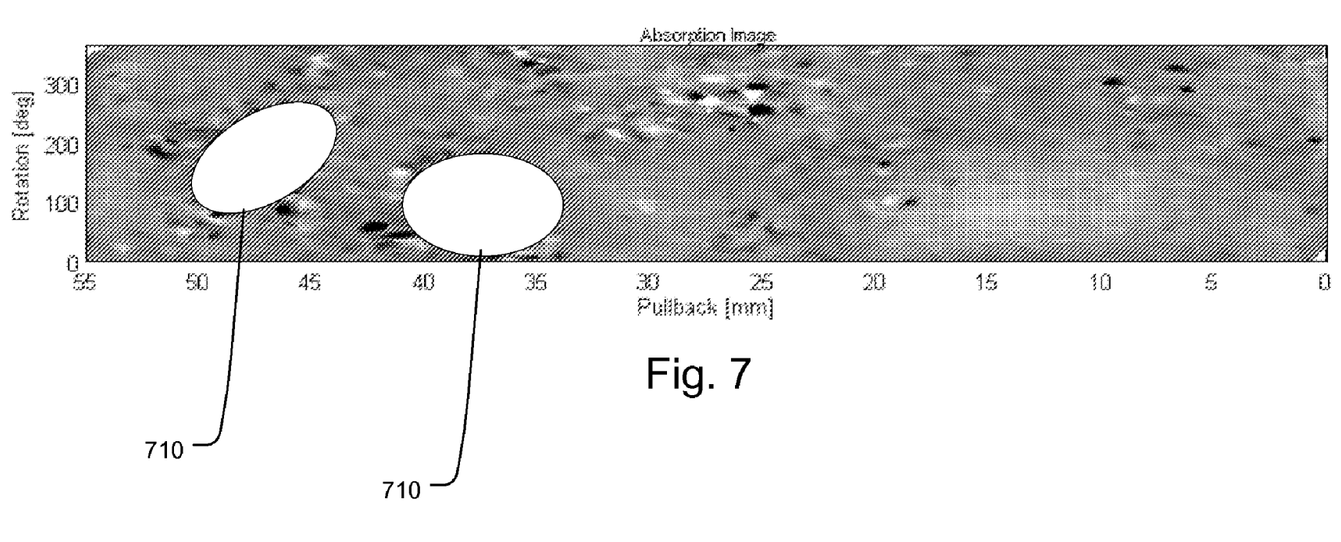
FIG. 7 is a false color absorption image highlighting potential thrombi.

FIG. 7 illustrates one example of an image provided on the display device of the user interface 70. This is processed absorption spectra in which areas of potential thrombi are identified as described in FIG. 4, for example. These regions are then highlighted with false color 710 in order to convey the result of the thrombus detection to the operator.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for locating a vascular obstruction within a vessel, the method comprising:
   determining spectral responses of a wall of the vessel through an intervening fluid by inserting a catheter into the vessel, irradiating the wall of the vessel via a head of the catheter and detecting returning light while rotating the head within the vessel and drawing the head through the vessel to generate, from the returning light, a spectral image of the wall comprising a plurality of pixels, and defining spatial regions of the spectral image relative to the rotation of the head and longitudinal position of the head in the vessel;
   calculating average spectral responses at multiple wavelengths for pixels within each of the spatial regions of the spectral image
   analyzing fluctuations in the measured spectral responses within each of the spatial regions by comparing a measured spectral response of each pixel within the region with at least one threshold derived from the average spectral response;
   locating the vascular obstruction based on the spatial fluctuations in the measured spectral responses by indentifying spatial regions in which the measured spectral responses exceed the threshold; and
   providing information indicating the location of the spatial region of the vascular obstruction to a user via a user interface.

2. The method of claim 1, wherein the step of determining the spectral responses comprises irradiating different regions with a near infrared source and detecting diffuse reflectance spectra within the different regions.

3. The method of claim 1, wherein the step of determining the spectral responses comprises irradiating different regions with a near infrared source and detecting absorption spectra within the different regions.

4. The method of claim 1, wherein the step of analyzing the fluctuations comprises analyzing spectral images covering a wavelength band in which lipids have a strong signal response.

5. The method of claim 1, wherein the step of analyzing the fluctuations comprises comparing the fluctuations to thresholds determined based on averages of the spectral response.

6. The method of claim 1, wherein the step of analyzing the fluctuations comprises determining a root mean square of spectral differences between the average spectral responses and the measured spectral responses.

7. A device for locating a vascular obstruction within a blood vessel, the device comprising:
   an optical catheter that is configured to be inserted into the blood vessel, the optical catheter irradiating the wall of the vessel via a head of the catheter and detecting returning light while the head rotates within the blood vessel and is drawn through the vessel to generate, from the returning light, a spectral image of the blood vessel wall comprising a plurality of pixels;
   a spectrometer configured to generate light into and receive light from the optical catheter to resolve spectral responses of walls of the blood vessel;
   an analyzer configured to receive the spectral responses and search for regions exhibiting spatial fluctuations in the spectral responses to locate vascular obstructions by (a) calculating average spectral responses of the pixels at multiple wavelengths, (b) deriving at least one threshold from the average spectral responses, (c) analyzing fluctuations in the measured spectral responses within spatial regions of the spectral image by comparing a measured spectral response of each pixel within each region with the threshold, and (d) determining a location of the vascular obstruction from the regions in which the measured spectral responses exceed the threshold; and
   a user interface that provides the location of the vascular obstructions to a user.

8. The device of claim 7, wherein the spectrometer comprises a near infrared source and a detector system for detecting diffuse reflectance spectra within the different regions.

9. The device of claim 7, further comprising a pullback and rotation unit for rotating and moving the head of the catheter through the blood vessel to determine the spectroscopic responses of the walls from the returning light from of the walls.

10. The device of claim 7, wherein the analyzer operates on the spectral responses only in a narrowed wavelength band.

11. The device of claim 7, wherein the analyzer operates on the spectral responses that only cover a wavelength band in which lipids have a strong signal response.

12. The device of claim 7, wherein the analyzer determines a root mean square of the spectral fluctuations between the pixels.

13. The method of claim 1, wherein the step of calculating the average spectral responses at the multiple wavelengths comprises calculating average spectral values for each of the regions and the step of analyzing spatial fluctuations in the spectral responses comprises comparing the measured spectral responses for multiple pixels within each region to the same average spectral responses; and then identifying regions in which the magnitudes calculated from the comparisons for multiple pixels exceed the threshold and locating the vascular obstructions to these regions.

14. The method of claim 13, further comprising:
fitting a polynomial function to the average spectral responses; and
the step of comparing the measured spectral responses comprises comparing the measured spectral responses to the polynomial function and calculating a root mean square of the differences between the measured spectral responses and the polynomial function to determine the magnitude of the comparison results.

15. The method of claim 1, wherein the at least one threshold comprises a lower threshold below the average spectral responses and an upper threshold above the average spectral responses, and wherein the step of indentifying regions in which the spectral values exceed the threshold comprises identifying pixels having measured spectral responses that extend beyond a band defined between the upper and lower thresholds.

16. The device of claim 7, wherein the at least one threshold comprises a lower threshold below the average spectral responses and an upper threshold above the average spectral responses, and wherein the step of determining a location of the vascular obstruction from the regions in which the measured spectral responses exceed the threshold comprises identifying pixels having measured spectral responses that extend beyond a band defined between the upper and lower thresholds.

\* \* \* \* \*